(12) United States Patent
Ellman et al.

(10) Patent No.: US 6,572,613 B1
(45) Date of Patent: *Jun. 3, 2003

(54) RF TISSUE PENETRATING PROBE

(76) Inventors: Alan G. Ellman, 1135 Railroad Ave., Hewlett, NY (US) 11557; Jon C. Garito, 1135 Railroad Ave., Hewlett, NY (US) 11557

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 55 days.

(21) Appl. No.: 09/760,522

(22) Filed: Jan. 16, 2001

(51) Int. Cl.⁷ .............................................. A61B 18/18
(52) U.S. Cl. .......................................... 606/45; 606/41
(58) Field of Search ............................. 606/41, 45, 48, 606/50, 49

(56) References Cited

U.S. PATENT DOCUMENTS

| | | | | |
|---|---|---|---|---|
| 4,289,132 A | * | 9/1981 | Rieman | 606/45 |
| 4,541,440 A | * | 9/1985 | Parsonnet | 607/132 |
| 5,571,101 A | * | 11/1996 | Ellman et al. | 606/45 |
| 5,733,282 A | * | 3/1998 | Ellman et al. | 606/45 |
| 5,741,250 A | * | 4/1998 | Garito et al. | 606/45 |
| 6,006,755 A | * | 12/1999 | Edwards | 128/898 |
| 6,044,846 A | * | 4/2000 | Edwards | 128/898 |

* cited by examiner

Primary Examiner—Michael Peffley

(57) ABSTRACT

An electrosurgical electrode comprises a generally L-shaped metal member comprising an electrically-insulated, shank part for mounting in a standard electrosurgical handpiece, and a generally straight part divided into first, second, and third sections, the first of which is electrically-insulating and the third of which is bare and terminates in a pointed end. The third section has an angled cross-section, such as rectangular, square or triangular, and more easily pentrates dense tissue targeted for radiofrequency thermal ablation. An important application is volumetric shrinkage of tongue base tissue, for example, for treating sleep disordered breathing.

8 Claims, 2 Drawing Sheets

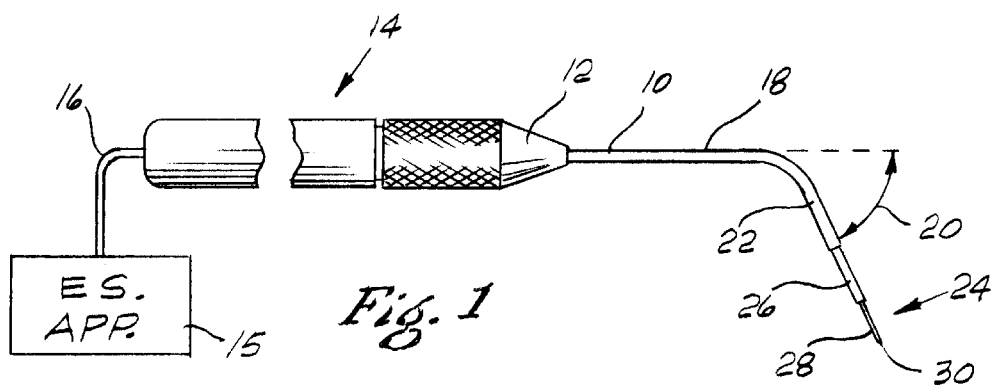
Fig. 1
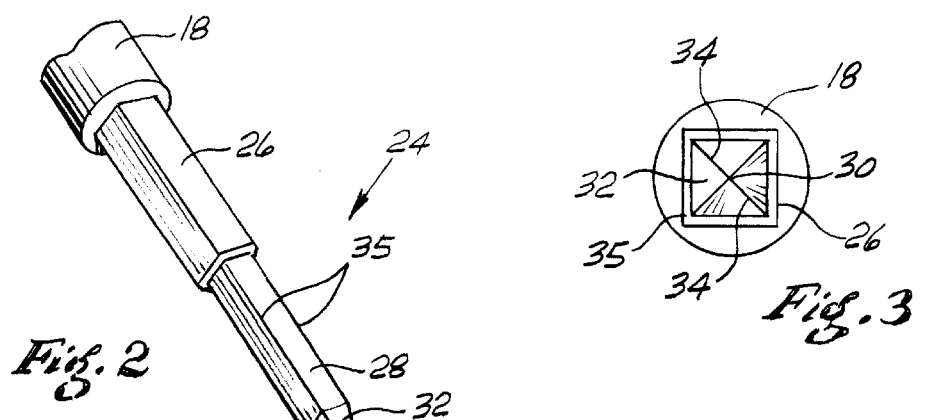
Fig. 2
Fig. 3
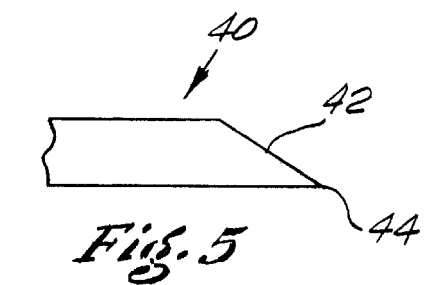
Fig. 5
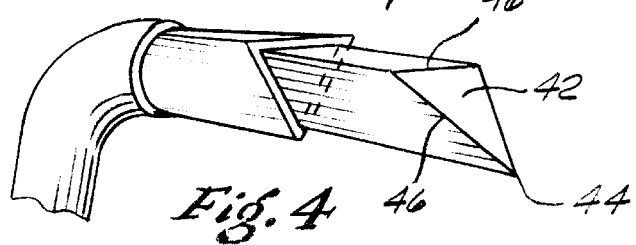
Fig. 4

RF TISSUE PENETRATING PROBE

This invention relates to a radio-frequency (RF) penetrating probe electrode for treating tissue with radio frequency energy, commonly referred to as electrosurgery.

BACKGROUND OF THE INVENTION

Our copending U.S. application Ser. No. 09/303,839, whose contents are hereby incorporated by reference, describes apparatus for use in a surgical procedure commonly known as minimally invasive surgery (MIS), for treating, say, a herniated disk to remove undesired regions and to provide controlled heat to shrink the tissue during surgery. The electrode for MIS use is preferably constructed with a flexible end controllable by the surgeon so as to allow the surgeon to manipulate the end as desired during the surgical procedure.

This tissue-shrinking concept has recently been extended to the treatment of other disorders. It is sometimes known as Radio Frequency Thermal Ablation (RFTA), which uses radio frequency (RF) heating to create targeted tissue ablation resulting in tissue volume reduction. One proposed application, described in a paper published in Kania, Sep. 25, 1999 by Pr. B. Meyer, is for the treatment of Obstructive Sleep Apnea Syndrome (OSAS) and more generally sleep disordered breathing (SDB). The proposed procedure is to insert a pointed electrode into the tongue base below the uvula and apply RF energy such that resistive heating of the tissue occurs, raising the temperature of the immediately surrounding tissue to a temperature that damages or kills the cells. This produces a small lesion which is later replaced by scar tissue and removed by the body, resulting in the shrinkage or volumetric reduction of the treated tissue. This procedure by reducing the volume of the local tissue may enlarge the airway alleviating SDB.

Present electrosurgical probes used for penetration of tissue for subcutaneous tissue reduction are typically round and generally terminate in an elongated thin tip portion which is inserted into and through tissue, such as, mucosal tissue, muscle epidermis, dermis, tonsil, turbinate, or tongue tissue. After the probe tip reaches the desired target area, RF electrosurgery energy passes through the probe to submucosaly create a lesion to shrink, ablate and volumetrically reduce the soft palate, tonsil, turbinate, uvula, or tongue, respectively. Our copending U.S. application Ser. No. 09/442,316, whose contents are hereby incorporated by reference, describes a generally L-shaped electrode for implementing RFTA, especially for tongue blade tissue. The electrode used has a round shape with a pointed end and a main feature is the addition of measured color-coded shaft sections for assisting the surgeon in determining needle pentration depth.

The use of the existing RF penetrating probes of this type is their inherent limitation and difficulty in penetration and moving through different tissue layers. The RF tissue reduction procedure with the existing probes slows down the procedure time. There is a loss of maneuverability, additional pre-operative pain to the patient due to the slow movement insertion through the tissue layers. The use of these existing probe designs produce a substantial amount of unnecessary pain and trauma to the patient. Other problems that often occur with the existing RF round probes is that, due to their elongated thin tip insertion portion, the tissue entry opening is wider causing additional trauma. Additionally, existing probes due to their poor design require unnecessary force to penetrate tissue.

SUMMARY OF THE INVENTION

An object of this invention is a new and useful improvement in the traditional electrosurgical probe of the type used for volumetric subcutaneous tissue reduction.

Another object of the invention is a new RF probe design that provides greater maneuverability, that speeds up the procedure time producing less trauma and pain to the patient, and that is less fatiguing for the surgeon.

In accordance with a feature of the present invention, an RF penetrating probe is changed from a round diameter with sharpened thin point to an angled shape which provides a sharper edge on the side or sides of the needle allowing it to create a much smaller hole upon penetration, requiring less force to develop the initial hole in the tissue, and less force to move through the tissue layers. The angled probe of the invention also concentrates the RF energy more efficiently and precisely, with the result that the RF energy radiosurgical apparatus can be lowered in wattage and in time to produce the desired subcutaneous volumetric tissue reduction effect.

In accordance with a further feature of the present invention, the RF penetrating probe has a tapered distal end that reduces to a point, but that tapered distal end has a triangular or rectangular cross-section with the edges forming the triangular or rectangular cross-section extending parallel to the long axis of the distal end and being sharpened.

Among the benefits of the present invention is that the novel electrode can be used with low voltage, low power electrosurgical apparatus for the purpose of implementing RFTA with a relatively simple, easily learned procedure.

As with the tongue base electrode of the copending application, the electrode may be a generally L-shaped metal member comprising an electrically-insulated, generally straight shank part for mounting in a standard electrosurgical handpiece, a generally needle-shaped part which is electrically-insulating, and which, as the active section, is bare and terminates in a pointed end, and with the angled sides. The shaft portion preceding the bare active end may incorporate the invention of the copending application and thus be divided into several sections that are dimensioned and constructed so as to enable the surgeon to know fairly precisely the depth of the active section in the targeted tissue.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals designating the same or similar elements.

BRIEF DESCRIPTION OF THE DRAWINGS

In the drawings:

FIG. 1 is a side view of one form of an electrode in accordance with the invention shown connected to electrosurgical apparatus;

FIG. 2 is an enlarged perspective view of the active end of the electrode of FIG. 1;

FIG. 3 is an end view of the electrode of FIG. 1;

FIG. 4 is an enlarged perspective view of the active end of a second embodiment of an electrode in accordance with the invention;

FIG. 5 is a side view of the electrode of FIG. 4;

DETAILED DESCRIPTION OF THE PREFERRED EMBODIMENTS

Figure 6:
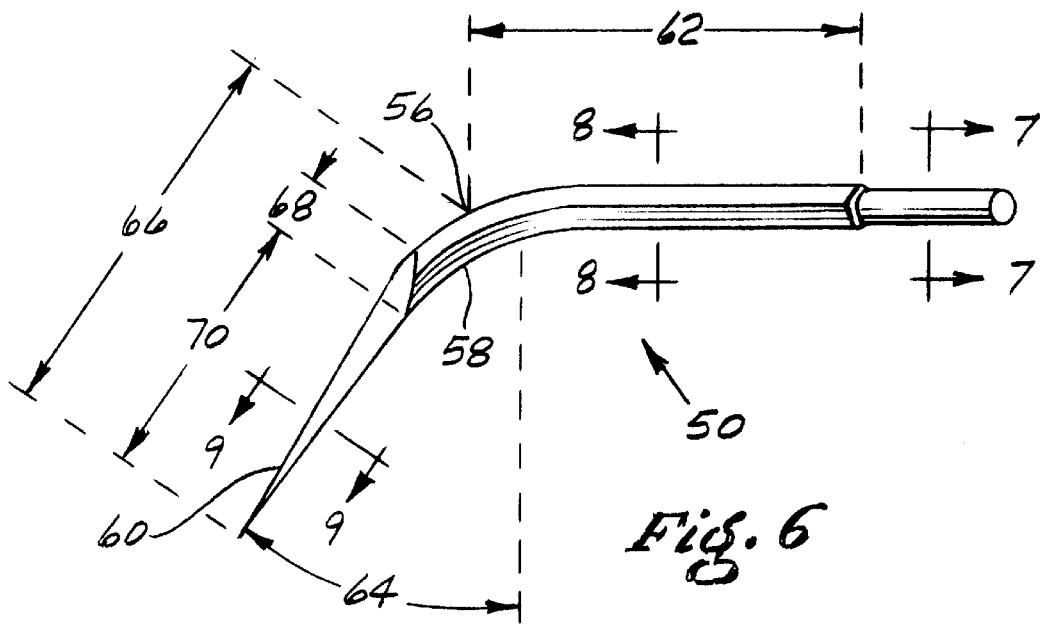
FIG. 6 is an enlarged side view of a third embodiment of an electrode in accordance with the invention.

The reader is directed to the referenced prior application and paper which will assist in understanding the improvements offered by the present application.

As mentioned, low-power, low-voltage electrosurgical apparatus can be used with the electrode of the invention. Such apparatus is available from Ellman International of Hewlett, N.Y. as Model IEC50. The handpiece that can be used is standard, available commercially. It typically comprises (see U.S. Pat. No. 5,571,101) an insulated barrel to be held by the surgeon with a collet type fitting for receiving the bare shank of an electrosurgical electrode. In a preferred embodiment of an electrode according to the invention illustrated in FIG. 1, the electrode 10 comprises, preferably, a one piece metal core that is bare at one end which is dimensioned to fit into and make electrical contact with the collet 12 of the handpiece 14 (shown schematically) whose cable 16 in turn is plugged into the electrosurgical apparatus 15. The straight (horizontal) shank part of the electrode is coated with a thick 18 coating of electrically-insulating material. The thickly-coated part then bends at about a 75° angle 20 to form another straight part 22 which includes an extension of the thickly-coated part which is then followed by a straight needle-shaped part 24 comprising a thinly-coated electrically-insulating section 26 (referred to in the claims as the first section) and a bare section 28 (referred to in the claims as the second section) with a sharply pointed end 30 (FIG. 2). The bare section 28 has a rectangular cross-section which tapers down 32 (referred to in the claims as the third section) to the pointed end 30. When "rectangular" is used herein, it is meant to include "square". Thus, the tapered section 32, which in this instance is square, also has a square cross-section, which also may be characterized as pyramidal. As a result, the point 30 is formed by the four surfaces of the pyramid 32 coming to a sharpened point 30 (FIG. 3). Those four surfaces, also ground down to form four longitudinal sharp edges 34, contribute to the improved penetration performance of the electrode of the invention, as do also the sharp corners 35. While in the FIG. 1 embodiment the shank 22 is shown as rectangular, since that part does not assist in the ability of the needle to penetrate tissue, it can also be round or with non-angled sides. While in the FIG. 1 embodiment the second bare section 28 is shown as rectangular, since that part does assist in the ability of the needle to penetrate tissue, it preferably has an angled cross-section. It is also possible for the tapered section 32 only to be angled, but it is preferred that the bare section 28 immediately preceding the tapered section 32 be angled also.

Figure 10:
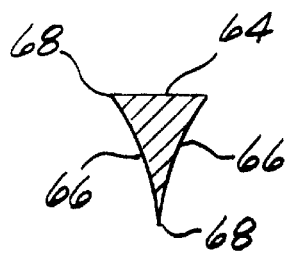
FIG. 10 is a cross-sectional view of a fourth embodiment of an electrode in accordance with the invention.

FIGS 4 and 5 show a modification in which the bare active section 40 has a triangular cross-section, and the front end 42 is tapered toward one of the triangle corners 44 which projects the furthest forward and serves as the needle point. The main penetration is effected by angled corners 46 which are again ground sharp. In the embodiment shown, the sides of the triangle are made up of flat surfaces. Thus, for an equilateral triangle, that means that the side angles (in the cross-section) are 60°. This is not essential. Those sides 66 can be concave, as illustrated at 64 in FIG. 10. Concave sides are preferred as it results in sharper angles at the corners 68, typically less than 60°. FIG. 10 also shows that the triangular cross-section need not be equilateral.

Figure 7:
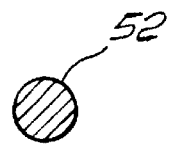
FIGS. 7, 8 and 9 are cross-sectional views taken along the lines 7—7, 8—8, and 9—9, respectively, of FIG. 6.
Figure 8:
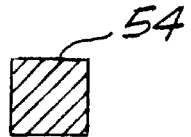
Figure 9:

FIGS. 6–8 show another angled electrode according to the invention. In this case, starting from square stock, the end 52 is ground round (see FIG. 7) and bare and fits the collet 12 of the handpiece. The next section 54 remains square (see FIG. 8) and is coated with an electrically-insulating coating. Next, the electrode bends at section 58, at an angle 64 of about 20° to form a straight tapered section 60 which is ground to be triangular and is ground down to a pointed end. The various cross-sectional changes are indicated in the sections of FIGS. 7–9. As an example, which is not to be considered to limit scope, the dimensions being in inches: section 54 has a length 62 of about 2.00; the length 66 of the section from the bend 56 to the point 61 is about 1.375; the length 68 of the square-triangular transition section following the bend is about 0.25; and the length 70 of the distal tapered section is about 0.70. The starting square stock had a side dimension of 0.0625.

Figure 11:
FIG. 11 is a cross-sectional view of a fifth embodiment of an electrode in accordance with the invention.

As a further possibility, though more difficult to make, the cross-section may be boat-shaped to form a rhomboid with parallel concave or convex surfaces forming sharp angles along the sides and pointed at the front. Also, longitudinal ridges may be provided on the concave or convex surfaces or both of this shape as well as along the other angled shapes, as this feature would decrease undesirable angular or rotational movements of the RF probe. One example is illustrated in FIG. 11 at 70.

The structure of the RF penetrating probe of the invention provide a sharper edge on each side of the needle allowing it to create a much smaller hole upon penetration and requires less force to develop the initial hole in the tissue, and less force to move through the tissue layers. It provides greater maneuverability, speeds up the procedure time producing less trauma and pain to the patient, and less fatigue for the surgeon. The angled probe also concentrates the RF energy at the angled sides more efficiently and precisely. It allows the radiosurgical apparatus to be lowered in wattage and in time to produce the desired subcutaneous volumetric tissue reduction effect. The thin coating of dielectric material over the penetrating surface of the probe except for the bare tip portion of the probe provides an important insulation of the non-active parts of the metal probe, which is contacting the area of every patient's skin when the RF energy is engaged for typically 5 to 30 seconds. The insulation material can be nylon, Teflon, or ceramic materials. The electrode is constructed to pass the RF energy to the subcutaneous target tissue at the uninsulated angled tip of the electrode. The shrinkage is intended to occur by the RF subcutaneous volumetric reduction of tissue contacted by the angled tip when the electrode is activated, not at the point of entry. Other known RF subcutaneous probes may damage the structural integrity of the tissues, or could cause or produce necrosis of the tissue with or without infection. The ease of penetration often depends on the mechanical factors and characteristics of tissue such as penetrability, density, elasticity and thickness. The angled needle of the invention is most effective with oral tissue or connective tissue which consists of pigmented tissues, collagen fibers, elastic fibers, or reticular fibers. The new angled RF subcutaneous probe could be made of stainless steel, tungsten, or other non-reactive, high-temperature metals. The new probe typically would be heat-treated, hardened and tempered. Diameters of the preferred needles range from 0.006 to 0.080 inches. The cross-sectional shape of the insulated sections of the RF probe shaft may be round or triangular or rectangular. The cutting edges of the RF probe preferably are ground and honed to provide edges that will cut through dense, difficult-to-penetrate tissue. The new RF subcutaneous probe with its angled cutting tip shape is results in better patient care and greater comfort and satisfaction for the surgeon.

The overall dimensions of the electrode 10 may be similar to that of the tongue base electrode described in the copending application Ser. No. 09/442,316, and may also include the feature of the addition of measured color-coded shaft sections for assisting the surgeon in determining needle penetration depth. For example, in the FIGS. 1 and 2 embodiment, the insulating first section 26 may be of a first color, and the following second bare section 28 of a second color, both of which are colored differently. If desired, the insulated section 26 can be subdivided into two or three sections of the same length, equal to that of the bare section 28, also of a different color, so that the surgeon can now tell by the visible color whether the electrode has penetrated into the tissue to be treated to any of three or four different depths, knowing the length of each of the differently colored sections. For ease of measuring penetration depth, four differently-colored sections can have the same length of about 1 cm. Preferably, the thin coating on the section 26 is formed by fused powdered Teflon having a thickness of about 0.002–0.008 inches, and the thicker coating 18, which is less critical, can be of heat-shrunk plastic tubing. The angle 20 preferably is maintained between about 60° and 90°. The point 26 at the bare end must be sufficiently sharp so that it can easily penetrate tongue base tissue as deep as necessary during the procedure without causing the electrode to unduly change its shape. The insulation of the thin electrically-insulating coating must be capable of not fracturing during the procedure to avoid RF leakage that could create ulceration, as well as being normally capable of resisting RF leakage when whole, yet must be sufficiently smooth so as not to create undue friction between it and the tissue as the electrode penetrates the tissue, and be able to withstand repeated use in puncturing and penetrating tissue. The fused Teflon powder has the necessary attributes to satisfy these requirements. The needle outside diameter must be small enough to enable easy penetration into the tissue yet large enough to withstand the flexing forces involved in the penetration. The sharpened end, again for easier penetration, preferably tapers to a sharp point over a distance of about 2–4 mm.

The surgical procedure is as follows. Only the steps relative to the invention are recited in broad terms. The unipolar handpiece 14 is connected in the usual way to the electrosurgical apparatus 15. If desired, the electrode handpiece may be shaped like a gun handle that can be held in the surgeon's hand. The electrode 10 is mounted in the handpiece 14 in the usual way. The surgeon inserts the electrode 10, pointed end 30 first, into the tissue to be treated, such as the tongue base of the patient as one example, to the desired depth. The surgeon then activates the electrosurgical apparatus 15 and electrode 10 choosing operating parameters such that relatively low power, low voltage settings of the apparatus are chosen. For the IEC50 instrument, which generates an output power of about 50 watts, a typical power setting of about 3–8 can be used. These values can be determined beforehand using test tissue, typically animal, and measuring the temperature due to resistive heating in the tissue surrounding the tip of the needle after a reasonable ON time of the instrument, say about 8–20 sec. The goal should be a tissue temperature between about 50° and 100° C., at which temperatures the tissue in a first area surrounding the inserted electrode section 28 carbonizes. When the needle electrode 10 is then withdrawn, scar tissue is formed which ultimately becomes absorbed by the body shrinking the tissue volume. This normally will enlarge the throat passageway alleviating, as an example, sleep disorder symptoms. In most instances, the tissue shrinkage will have to be increased before a sufficient reduction is accomplished, and the surgeon by examination will be able to judge how much will be needed. If more shrinkage would be required than can be obtained from a single treatment with, say, a 1 cm penetration, before or after the apparatus has been turned off and while the tissue remains heated or is allowed to cool down if desired, the surgeon presses down on the electrode 10 until it penetrates deeper, which means that the needle has now penetrated a total of, say, 2 cm. The surgeon now restarts the instrument for another 8–20 sec at the same settings. This time, the resistive heating occurs in a second area around the bare first section 28 now 2 cm deep into the tissue. No heating occurs around the penetrated electrically-insulating section 26, because it is adequately electrically-insulated and no electrosurgical currents flow into the tissue from that section. Thus the depth of the tissue damage is extended further into the tissue. The procedure can be repeated yet a third time by further penetrating the tissue up a further depth. Now the needle depth may be, say, approximately 3 cm, and a deeper region of the tissue is damaged with its subsequent shrinkage. In most cases, penetration up to 3 cm of tongue tissue is adequate to accomplish a significant reduction in the tissue volume and concomitant enlargement of the throat passageway.

The simplicity of the procedure is evident. The difference between the tissue shrinkage process and a typical electrosurgical cutting is that, with the latter, the surgeon uses the activated electrode for the shortest time possible while cutting to avoid extensive tissue damage, while, with the tissue shrinkage procedure, the active electrode stays in the tissue a reasonable time at each penetration to ensure that extensive tissue damage will occur, since it is only the damaged tissue that will shrink.

The insulating tube 18 will prevent accidental touching of patient tissue by the electrode sides, so that the electrosurgical curents are localized to the bare electrode end.

The apparatus used in the procedure preferably generates electrosurgical currents with a frequency of about 2.5–5 MHz, with about 4 MHz preferred. It is found that this frequency range provides a more controlled lesion size for greater reproducibility. It will also be appreciated that a higher-powered electrosurgical apparatus can also be used provided that a lower power setting is chosen to keep the power level below about 50 watts. In the preferred example, the apparatus HEMO setting is preferably chosen as it produces a partially-rectified RF waveform for reduced cutting.

While the electrode described has particular utility for shrink tongue base tissue, it will be appreciated that it may also be of use for shrinking other tissue when such tissue may be causing blockage or obstruction of bodily functions. Another example is the shrinking of spine tissue as described in the referenced and incorporated copending patent application Ser. No. 09/303,839, now U.S. Pat. No. 6,231,571. In that application, an electrode configuration employing two side-by-side bipolar electrodes in a flexible handpiece end is employed for removing undesired regions of a herniated disc with the advantage that the electrosurgical currents are restricted to the region between the electrodes. FIG. 12 of the present application is a perspective view similar to FIG. 2 based on the disclosure and drawings, particularly FIG. 6 of the referenced patent, illustrating a bipolar version of the angled electrode of the present invention. In FIG. 12, two side-by-side pointed angular electrodes 24' each comprising a bare section 28' coming to a sharpened point 30' is provided at the handpiece end. As described in the incorporated patent, the two electrode 24' are separated by an insulating layer 80 such that when the points are introduced into the tissue to be shrunk and a bipolar voltage applied across the two electrodes 24', the resultant electrosurgical currents are confined to the vicinity of the two electrodes 24'. This embodiment is also obviously applicable to shrinking tongue base tissue as described in the other incorporated referenced patent application.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical electrode for volumetric shrinkage of tissue comprising:
   (a) an electrically-conductive member comprising a shank portion having at a first end means for connecting to electrosurgical apparatus and having at a second end an electrode portion comprising a tip that has a sharpened point adapted for penetrating tissue,
   (b) the electrode portion adjacent the tip being generally straight and needle-shaped and comprising, in order, an electrically-insulated first, a bare second, and an active third tip section located at the end of the shank portion furthest removed from the first end,
   (c) the active third tip section being bare so as to allow electrosurgical currents to enter penetrated tissue when the electrosurgical apparatus is activated,
   (d) the first section having a thin electrically-insulating coating so as to prevent electrosurgical currents to enter tissue penetrated by the third section when the electrosurgical apparatus is activated,
   (e) the active third tip section having a non-round angled cross-section terminating in sharpened point,
   (f) the active third tip section being tapered and having longitudinal ribs extending along sides of the taper.

2. An electrosurgical electrode for volumetric shrinkage of tissue comprising:
   (a) an electrically-conductive member comprising a shank portion having at a first end means for connecting to electrosurgical apparatus and having at a second end an electrode portion comprising a tip that has a sharpened point adapted for penetrating tissue,
   (b) the electrode portion adjacent the tip being generally straight and needle-shaped and comprising, in order, an electrically-insulated first, a bare second, and an active third tip section located at the end of the shank portion furthest removed from the first end,
   (c) the active third tip section being bare so as to allow electrosurgical currents to enter penetrated tissue when the electrosurgical apparatus is activated,
   (d) the first section having a thin electrically-insulating coating so as to prevent electrosurgical currents to enter tissue penetrated by the third section when the electrosurgical apparatus is activated,
   (e) the active third tip section having a non-round angled cross-section terminating in sharpened point,
   (f) wherein the electrode portion comprises a round section at its first end, a triangular section at its third section and a rectangular section between its first end and its third section.

3. A procedure for treating tissue to cause volumetric shrinkage of the tissue, comprising the steps:
   i) providing electrosurgical apparatus connected to an electrosurgical electrode for radiofrequency thermal ablation, said electrosurgical electrode comprising:
      (a) an electrically-conductive member comprising a shank portion constituted of metal and having at a first end means for connecting to electrosurgical apparatus and having at a second end an electrode portion comprising a tip that has a sharpened point adapted for penetrating tissue,
      (b) the electrode portion adjacent the tip being generally straight and needle-shaped and comprising, in order, an electrically-insulated first, a bare second, and an active third tip section located at the end of the shank portion furthest removed from the first end,
      (c) the active third tip section being bare so as to allow electrosurgical currents to enter penetrated tissue when the electrosurgical apparatus is activated,
      (d) the first section having a thin electrically-insulating coating so as to prevent electrosurgical currents to enter tissue penetrated by the third section when the electrosurgical apparatus is activated,
      (e) the active third tip section having a non-round angled cross-section terminating in the sharpened point,
   (ii) penetrating the tissue to be treated with the active tip section having the sharpened point to a desired depth,
   (iii) activating the electrosurgical apparatus to provide at the third section low voltage, low power electrosurgical currents until the tissue adjacent the sharpened point is sufficiently damaged to cause volumetric shrinkage of the treated tissue,
   (iv) thereafter pushing the active tip section deeper into the tissue and re-activating the electrosurgical apparatus to provide at the third section low voltage, low power electrosurgical currents until the new tissue adjacent the sharpened point is sufficiently damaged to cause deeper volumetric shrinkage of the treated tissue.

4. The procedure of claim 3, wherein the electrosurgical apparatus generates electrosurgical currents with a frequency of about 2–4 MHz.

5. The procedure of claim 3, wherein the tissue being treated is in the throat for the purpose of shrinking the tissue to treat a sleeping disorder.

6. A procedure for treating sleep disordered breathing as claimed in claim 3, wherein step ii) is carried out until the second section is fully inserted into the tissue, and step iv) is carried out until the first section is fully inserted into the tissue.

7. A procedure for treating sleep disordered breathing as claimed in claim 3, wherein a surgeon is carrying out the procedure, the first and second sections of the electrosurgical electrode of the electrosurgical apparatus provided in step i) are differently colored, and step ii) is carried out until the color of the second section is no longer visible to the surgeon.

8. A procedure for treating sleep disordered breathing as claimed in claim 7, wherein step iv) is carried out until the color of the first section is no longer visible to the surgeon.

* * * * *